US005777905A

United States Patent [19]
Dowdle et al.

[11] Patent Number: 5,777,905
[45] Date of Patent: Jul. 7, 1998

[54] OBSTETRICAL AND GYNECOLOGICAL EVENT AND STATUS CALCULATOR

[75] Inventors: Mark A. Dowdle, Burley, Id.; Wm. Dean Wallace, Salt Lake City; Christopher A. Cutler, Centerville, both of Utah

[73] Assignee: Clinical Innovations Associates, Inc., Murray, Utah

[21] Appl. No.: 425,098

[22] Filed: Apr. 20, 1995

[51] Int. Cl.⁶ .................. G06F 3/00; A61B 10/00
[52] U.S. Cl. .................. 364/709.12; 128/738
[58] Field of Search ............ 364/709.02, 709.06, 364/708.01, 709.12, 413.12, 705.1, 413.01, 413.02, 413.03; 283/2; 235/88 RC; 128/738

[56] References Cited

U.S. PATENT DOCUMENTS

| 4,370,727 | 1/1983 | Bellet ........................ 364/705 |
| 4,443,851 | 4/1984 | Lin ........................... 364/415 |
| 4,591,974 | 5/1986 | Dornbush et al. ............. 364/200 |
| 4,754,418 | 6/1988 | Hara ......................... 364/708 |
| 5,496,070 | 3/1996 | Thompson .................... 283/2 |

OTHER PUBLICATIONS

Berlex Laboratories, Inc. –Electronic device for determining due dates (photocopy), 1988.
Enfamil –birth wheel (photocopy).
Tokos Medical Corporation –birth wheel (photocopy).
Fujisawa –Smith Kline Laboratories–birth wheel (photocopy).
Corometrics Medical Systems, Inc. –birth wheel (photocopy).

*Primary Examiner*—Chuong Dinh Ngo
*Attorney, Agent, or Firm*—Trask, Britt & Rossa

[57] ABSTRACT

An electronic calculator is disclosed for calculating important obstetrical dates based on the entry of certain variables or information. The electronic calculator is structured to accept input relating to the last menstrual period, conception date, estimated date of confinement and estimated gestational age. The entry of any one of these variables of information, along with the entry of a reference date, allows the calculator to calculate the other, remaining variables. The electronic calculator provides information similar to that conventionally obtained from an obstetric wheel or birth wheel, but additionally provides for the capability of recalculating and updating the obstetric dates based on new or additional information input into the calculator. The dates calculated using the invention are, therefore, more accurate and can be stored in memory for recall at each subsequent obstetrical visit. The calculator can also be used to calculate and schedule future dates for testing or observance based on the input and calculated variables.

25 Claims, 8 Drawing Sheets

FRONT SIDE

GESTATIONAL AGE/LENGTH/WEIGHT TABLE

| EGA (WEEKS) | AVERAGE FETAL LENGTH (cm) | (in.) | AVERAGE FETAL WEIGHT (gm) | (Lb. | oz.) |
|---|---|---|---|---|---|
| 8 | 4 | 1.6 | 1 | < | 1 |
| 9 | 4 | 1.6 | 2 | < | 1 |
| 10 | 6.5 | 2.6 | 4 | < | 1 |
| 11 | 6.5 | 2.6 | 7 | < | 1 |
| 12 | 9 | 3.5 | 14 | < | 1 |
| 13 | 9 | 3.5 | 25 | 0 | 1 |
| 14 | 12.5 | 4.9 | 45 | 0 | 1 |
| 15 | 12.5 | 4.9 | 70 | 0 | 2 |
| 16 | 16 | 6.3 | 100 | 0 | 3 |
| 17 | 16 | 6.3 | 140 | 0 | 5 |
| 18 | 20.5 | 8.1 | 190 | 0 | 7 |
| 19 | 20.5 | 8.1 | 240 | 0 | 10 |
| 20 | 25 | 9.8 | 300 | 0 | 10 |
| 21 | 25 | 9.8 | 360 | 0 | 13 |
| 22 | 27.5 | 10.8 | 430 | 0 | 15 |
| 23 | 27.5 | 10.8 | 501 | 1 | 2 |
| 24 | 30 | 11.8 | 600 | 1 | 5 |
| 25 | 30 | 11.8 | 700 | 1 | 9 |
| 26 | 32.5 | 12.8 | 800 | 1 | 12 |
| 27 | 32.5 | 12.8 | 900 | 2 | 0 |
| 28 | 35 | 13.8 | 1001 | 2 | 4 |
| 29 | 35 | 13.8 | 1175 | 2 | 9 |
| 30 | 37.5 | 14.8 | 1350 | 3 | 0 |
| 31 | 37.5 | 14.8 | 1501 | 3 | 5 |
| 32 | 40 | 15.7 | 1675 | 3 | 11 |
| 33 | 40 | 15.7 | 1825 | 4 | 0 |
| 34 | 42.5 | 16.7 | 2001 | 4 | 7 |
| 35 | 42.5 | 16.7 | 2160 | 4 | 12 |
| 36 | 45 | 17.7 | 2340 | 5 | 2 |
| 37 | 45 | 17.7 | 2501 | 5 | 9 |
| 38 | 47.5 | 18.7 | 2775 | 6 | 2 |
| 39 | 47.5 | 18.7 | 3001 | 6 | 10 |
| 40 | 50 | 19.7 | 3250 | 7 | 3 |
| 41 | 50 | 19.7 | 3501 | 7 | 12 |
| 42 | 52.5 | 20.7 | 4001 | 8 | 14 |
| 43 | 52.5 | 20.7 | 4501 | 9 | 15 |

NOTE: FIGURES GIVEN ARE AVERAGES. THE NORMAL INDIVIDUAL MAY VARY WIDELY, PARTICULARLY AT TERM OR AFTER.

120

BACK SIDE

WEEKLY GESTATIONAL DEVELOPMENT

WK.
1. EARLY DEVELOPMENT OF OVARIAN FOLLICLE (EGG).
2. EGG DEVELOPMENT COMPLETE. EGG RELEASED DAY 13-15.
3. FERTILIZATION DAY 14-16. FIRST CELL DIVISION 30 HOURS LATER. 16 CELLS AT 72 HOURS. IMPLANTATION ON DAY 20-21.
4. BEGINNING OF EMBRYO AND PLACENTA.
5. MENSTRUAL PERIOD MISSED. HEART TUGES BEGIN. THYROID AND NERVE DEVELOPMENT BEGIN. FETAL BLOOD CELLS STARTS FORMING. POSITIVE PREGNANCY TEST.
6. HEART BEGINS TO BEAT. DEVELOPMENT BEGINS OF EYES, EARS, ARM AND LEG BUDS, AND LUNGS.
7. DEVELOPMENT BEGINS OF MOUTH, NASAL PIT, AND LIVER.
8. UPPER LIP FORMED. ARMS BEND. PALATE DEVELOPING. FETAL MOVEMENT STARTS.
9. EYELIDS, ELBOW, EXTERNAL EAR, BONES AND GENITAL FORMATION BEGINS.
10. DISTINCT FINGERS AND TOES. OVARIES AND TESTES DISTINGUISHABLE. ALL STRUCTURES ARE NOW PRESENT IN BEGINNING STAGES. HEART FUNCTIONS.
11. EYELIDS CLOSED. HEAD MORE ROUNDED.
12. FACE HAS PROFILE WITH CHIN. PENIS OR CLOTORIS FORMS.
13. INTESTINES DEVELOPING. EARLY FINGERNAIL DEVELOPMENT.
14. EXTERNAL GENITALIA DISTINGUISHABLE. WELL DEFINED NECK.
15. FETUS KICKS, TURNS HEAD, SWALLOWS AND SQUINTS.
16. HEAD ERECT. VOCAL CORDS FORMED. FIRST FETAL MOVEMENTS FELT (QUICKENING) 16-20 WEEKS. SEX IDENTIFIABLE.
17. LOWER LIMBS WELL DEVELOPED.
18. EARS STAND OUT FROM HEAD.
19. DOWNY LANUGO (FINE HAIR) COVERS BODY.
20. MIDPOINT OF PREGNANCY.
21. VERNIX PRESENT (GREASY COATING ON BABY'S SKIN).
22. HAIR ON HEAD AND BODY.
23. FAT BENEATH SKIN INCREASES.
24. SKIN WRINKLED AND RED.
25. FINGERNAILS PRESENT. FETUS VIABLE.
26. EYEBROWS AND EYELASHES.
27. BUDS FORM FOR TEETH.
28. PUPILARY MEMBRANE DISAPPEARS FROM EYES. FETUS HICCUPS.
29. EYES SENSITIVE TO LIGHT.
30. EYES REOPEN. HEAD HAIR INCREASES.
31. SKIN SLIGHTLY WRINKLED.
32. TOENAILS PRESENT. BODY FILLING OUT.
33. TESTES DESCENDING. FETUS GROWING RAPIDLY.
34. FINGERNAILS REACH FINGER TIPS.
35. SKIN PINK AND SMOOTH.
36. GAINS 1/2 POUND PER WEEK. KIDNEYS MATURE.
37. LUNGS MATURE.
38. TOENAILS REACH TOE TIPS.
39. PROMINENT CHEST. BREASTS PROTRUDE.
40. EXPECTED DELIVERY DATE. FINGERNAILS BEYOHND FINGER TIPS.
41. GROWTH SLOWS.
42. THIN DRY PARCHMENT-LIKE SKIN.
43. DECREASED AMNIOTIC FLUID.

OBSTETRICAL AND GYNECOLOGICAL EVENT AND STATUS CALCULATOR

BACKGROUND

Field of the Invention

The present invention relates to devices for determining the existence or future occurrence of various events which relate to the pregnancy or gestational term in humans. Specifically, the present invention relates to electronic calculator means for determining such events.

Statement of the Relevant Art

In the course of a woman's pregnancy, a number of calendar events and fetal status determinations are calculated by obstetrician/gynecologists ("OB/GYN"), such as the expected date of birth. The establishment of such dates is important so that proper tests can be scheduled and so that the doctor can determine if the mother and child are progressing in the pregnancy within certain parameters of normalcy. The most significant dates during a pregnancy term include the beginning date of the last menstrual period, the date of conception, the estimated date of confinement (date of birth) and estimated gestational age of the fetus. With those dates established, the attending physician can accurately follow the patient's progress and prescribe treatment accordingly.

The medical profession has historically used what is called an obstetric wheel to calculate the important dates relating to pregnancy. Many obstetric wheels have been designed and manufactured, but each comprises the same basic elements. An obstetric wheel generally comprises a first wheel or card on top of which is attached a second, round wheel which is rotatable relative to the first wheel or card. The first wheel is imprinted with 365 increments corresponding to the 365 days of an average calendar year, and is further divided into and imprinted with the months of the year. The second round wheel is imprinted along its periphery with at least 40, and sometimes as many as 43, equally spaced marks corresponding to the 40-week average gestational period of a human fetus. A large indicator arrow is imprinted on the periphery of the second wheel immediately preceding the indicator mark for week 1, and at a distance therefrom equating to a week.

Further information may be printed on the second round wheel, usually in the form of concentric circles about the center axis of the card. The concentric circles are also typically divided into equally spaced segments corresponding to increments of information which change over the gestational period of the fetus. For example, one concentric circle may be divided into increments of weight, either in grams or pounds/ounces, or both, and may be imprinted with increasing measurements of fetal weight over the 40 week gestational period. As another example, one concentric circle may be divided into increments corresponding to increasing centimeter measurements of fetal length over the 40 week period. Some obstetric wheels may also indicate an average incremental increase of the mother's abdomen measured in centimeters over the 40 week period.

In use, the second round wheel is rotated relative to the first wheel until the large indicator mark on the periphery of the second round wheel is positioned to point to the day of the week in the next preceding month when the patient's menstrual cycle began. At the indicator mark corresponding to week 2 on the second round wheel, an indicator mark appears which is labelled "Conception." Hence, by knowing the day on which the patient's last period began (e.g., January 5), the obstetric wheel can be used to determine the approximate date of conception (e.g., January 19) and can determine that the due date of the child may be approximately 40 weeks hence (e.g., October 11). When the second round wheel is aligned as previously described, based on the beginning date of the last period, the other concentric circles of the second round wheel may be consulted to determine what the typical weight or length of the fetus is at any given time during the gestational period.

Obstetric wheels of the type previously described have limited usefulness in determining the important dates of pregnancy. Such wheels are limited essentially to three pieces of information which may be used to determine important dates. That is, only the beginning date of the patient's last period, the suspected date of conception, or the date upon which the patient first feels the fetus kick (which generally occurs at 20 weeks) may be used to position the obstetric wheel. Other relevant and measurable information which is determinative of gestational periods cannot be used with the obstetric wheel. Further, the information which can be used with the obstetric wheel is often inaccurate, or only approximated.

Therefore, it would be advantageous in the care of maternity patients to have means for determining important dates and events of pregnancy based not only on the traditional types of information relating to menstrual cycles, but also on other, more accurately measurable information. Additionally, it would be advantageous in the art to provide a device for determining important dates and events which additionally has the capability of storing such information for recall, and which has additional related capabilities, such as determining and storing dosages for medicine, for example.

SUMMARY OF THE INVENTION

In accordance with the present invention, an electronic calculator is structured with electronic calculation and memory capabilities for accepting input information relating to a patient's pregnancy to automatically calculate other relevant dates relating to the pregnancy. A number of variables may be used as the input information, including both calendar information and empirical test results, to calculate any other number of important dates relating to a gestational term. The electronic calculator of the present invention is also capable of storing information relating to a particular patient's medical profile which may be recalled at will. The electronic calculator is preferably structured to be small and readily portable.

The electronic calculator of the present invention is programmed to accept any one or more of five relevant dates, or variables, for calculating the other important dates of the gestational period. The five relevant dates or variables are 1) the estimated date of confinement (also referred to herein as "EDC"), 2) the first day of the last menstrual period (also referred to herein as "LMP"), 3) the date of conception or ovulation (also referred to herein as "CD"), 4) the reference date (also referred to herein as "RD"), and 5) the estimated gestational age (also referred to herein as "EGA"). By entering at least one of those variables into the calculator, the other variables may be calculated and stored. Then, based upon the five determined variables, other important dates, such as dates for conducting standard tests, can be determined.

The electronic calculator of the present invention may be programmed with a 100 year calendar which includes leap years, thereby improving the accuracy of date calculations. Many, if not most, obstetric wheels have no capability for taking into account the extra day in a leap year and are, therefore, inaccurate. The electronic calculator is also programmed with the capability of averaging together two determinations for a given variable to give a more accurate calculation of other important dates. For example, an EGA calculated from the input of other variables and an EGA which is determined by empirical testing can be averaged together to provide a more accurate date. The electronic calculator is similarly capable of accommodating variation in menstrual cycles.

In addition to the input, program and memory features of the invention, the electronic calculator includes a four function calculator (i.e., numerical keypad and function keys for addition, substraction, multiplication and division), a 24-hour clock and a calendar. In a preferred commercial embodiment, the calculator is housed within a compact case sized for insertion within a pocket or purse, and has room for accommodating additional written materials, including operating instructions, a gestational age-weight-length table, a chart of fetal development by week and a schedule of special procedural tests to be performed in various weeks of the pregnancy. The electronic calculator includes a solar-powered means and battery for operating the calculator.

BRIEF DESCRIPTION OF THE ILLUSTRATIONS

In the drawings, which illustrate what is currently considered the best mode for carrying out the invention, FIG. 1 is a schematic representation of the general operating steps of the present invention, including sample displays for each of the input variables, the current date, time and mathematical displays;

FIG. 5 is an enlarged view of reference materials which may be placed in the carrying case shown in FIG. 3;

DETAILED DESCRIPTION OF THE ILLUSTRATED EMBODIMENTS

The electronic calculator of the present invention may be adapted for use in determining the important obstetrical dates of virtually any animal pregnancy or gestation. For the sake of simplicity, however, the invention is described hereinafter in terms of use for humans.

Figure 1:
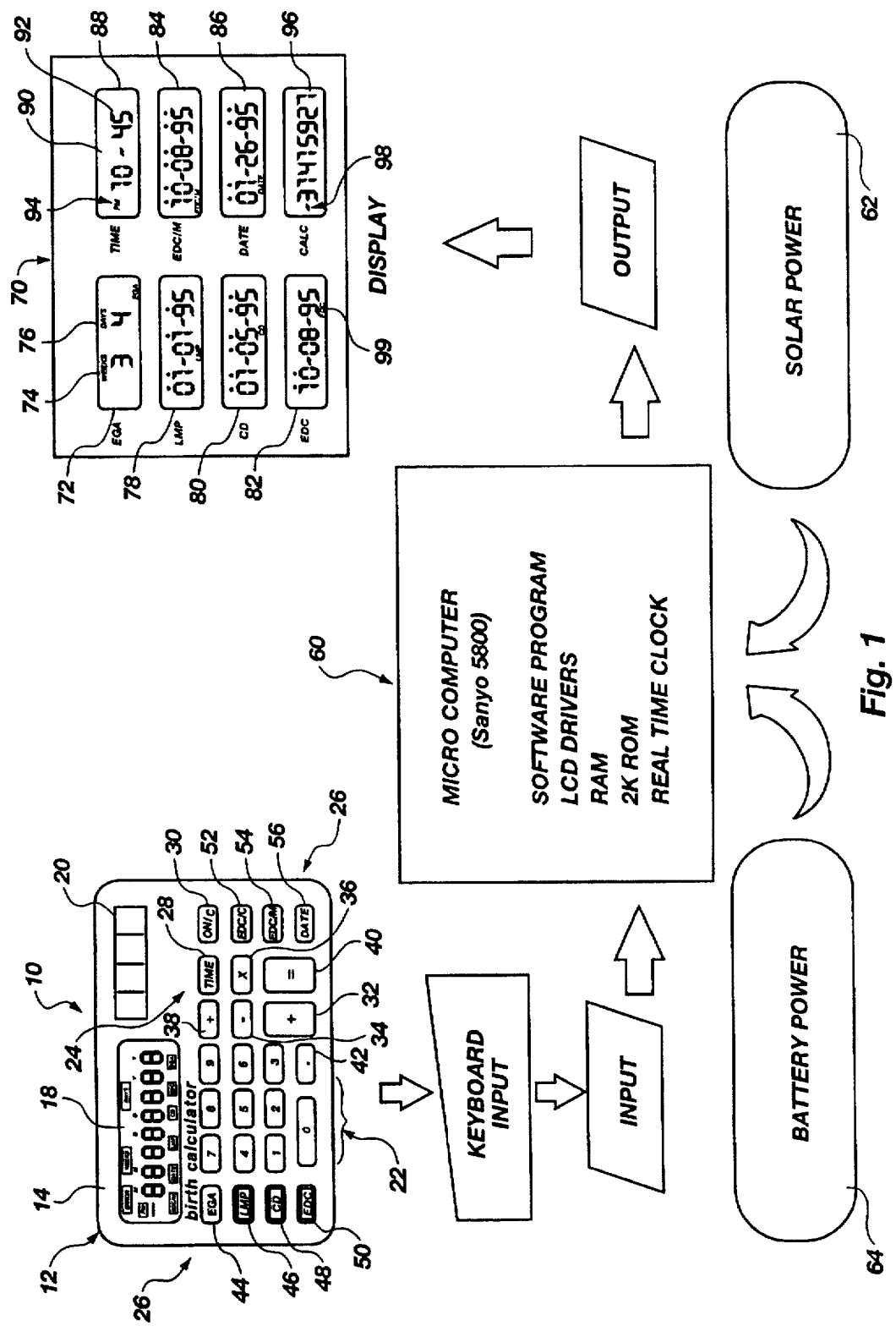

FIG. 1 generally illustrates the obstetrics calculator 10 of the present invention, and the electronic features of the invention. The calculator 10 includes a housing 12 having a front panel 14 bearing the displays and keys of the calculator 10 and a back panel 16 (seen in FIG. 4). The front panel 14 presents an LCD display window 18, a solar power panel 20 containing solar power means and battery (not shown), a keypad 22 bearing numbers 0–9, mathematical function keys, generally at 24, variable function keys, generally at 26, a time display function key 28 and a power/clearance ("ON/C") key 30. The mathematical function keys include an addition ("+" symbol) key 32, a subtraction ("−" symbol) key 34, a multiplication key ("×" symbol) 36, a division key ("÷" symbol) 38, a summation key ("=" symbol) 40, and a decimal point key 42.

The variable function keys 26 include an "estimated gestational age" (EGA) key 44, a "last menstrual period" (LMP) key 46, a "conception date" (CD) key 48, an "estimated date of confinement" (EDC) key 50, an "estimated date of confinement/clearance" (EDC/C) key 52, an "estimated date of confinement/memory" (EDC/M) key 54 and a "reference date" (DATE) key 56.

As represented generally at 60, the microcomputer of the calculator 10 includes a microprocessor such as a Sanyo 5800 series microprocessor (e.g., Sanyo No. LC 5372N) programmed as described further hereinafter, LCD (liquid crystal diode) display drivers, at least one RAM (random access memory), a 2K (kilobyte) ROM ("read only memory") and a real time clock. The calculator 10 may be powered by solar energy, represented at 62, and by battery power, represented at 64. The calculator 10 is powered by both means in the alternative as required by operating times, conditions and locales.

FIG. 1 also illustrates, generally at 70, the typical displays that may be viewed in output form responsive to the selection of any of the variable function or time keys. For example, the EGA 72 is displayed in terms of a number of weeks 74 and a number of days 76. The LMP 78, CD 80, EDC 82, EDC/M 84, and reference date 86 each are displayed in terms of a two digit month, two digit day and two digit year. The time 88 is displayed in hours 90 and minutes 92, with an additional meridiem display 94 indicating if it is "PM". If no meridiem display 94 is illuminated, it is assumed to be ante meridiem ("AM"). Alternatively, an "AM" icon may be provided. The mathematical display 96 is capable of displaying up to eight digits, including a decimal point display capability and the display of a "negative" ("−") symbol 98 indicating negative sums or entries. When any variable function key 26 is pressed, an icon 99 is also displayed to indicate which variable is being viewed (e.g., EDC, LMP, CD, EGA, DATE, etc.).

Figure 2A:
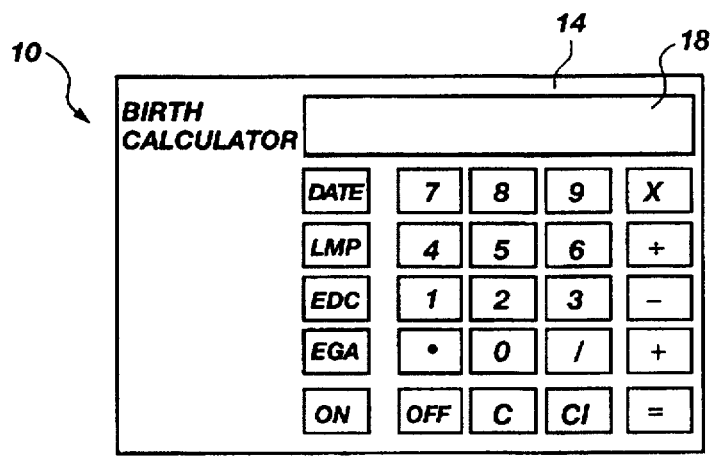
FIGS. 2(a–c) are exemplar embodiments of the invention illustrating various display mode configurations.
Figure 2B:
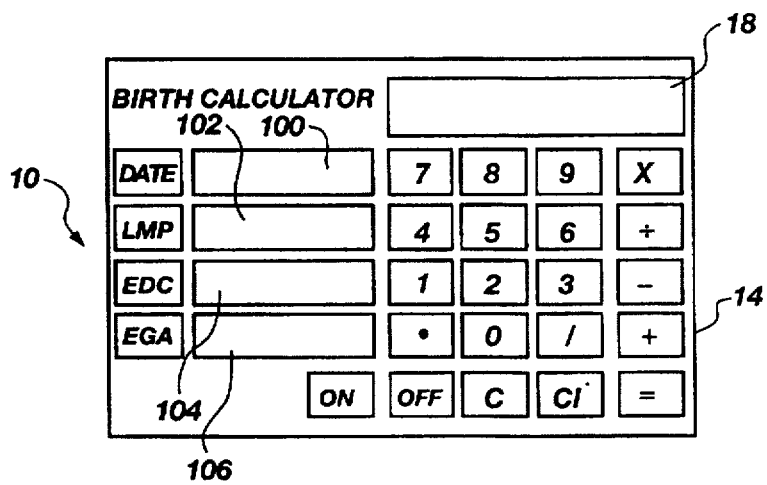
Figure 2C:
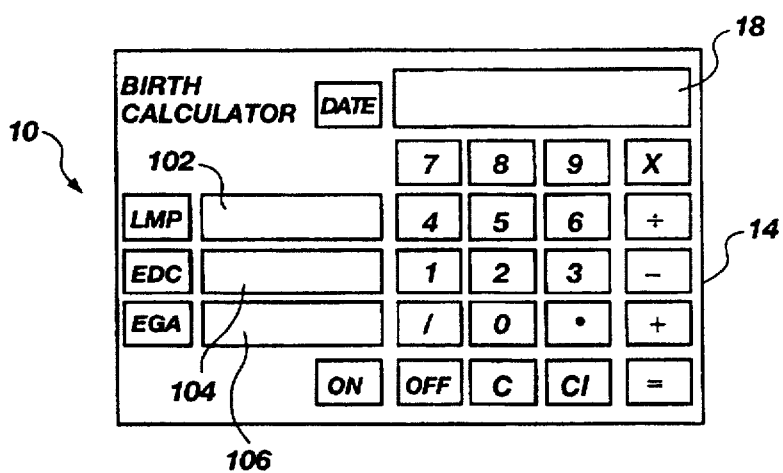

FIGS. 2(a–c) illustrate various embodiments of the front panel 14 of the calculator 10 where one or more displays may be included. In FIG. 2(a), the front panel 14 of the calculator 10 has a single LCD display 18 which will display all output information, including variables information, date, time and mathematical calculations. FIG. 2(b) illustrates an alternative front panel 14 configuration in which a main LCD display 18 is used to display output corresponding to time, mathematical calculations, and other certain dates; however, additional individual LCD displays are provided for displaying output information corresponding to the reference date 100, the LMP 102, the EDC 104 and the EGA 106. In a third alternative front panel 14 configuration depicted in FIG. 2(c), the main LCD display 18 is used to display the reference date, the time, certain variable information and mathematical calculations, and individual LCD displays are provided for output information corresponding to the LMP 102, the EDC 104 and the EGA 106. Other alternative configurations of the front panel 14 of the calculator may be adapted from those illustrated.

Figure 3:
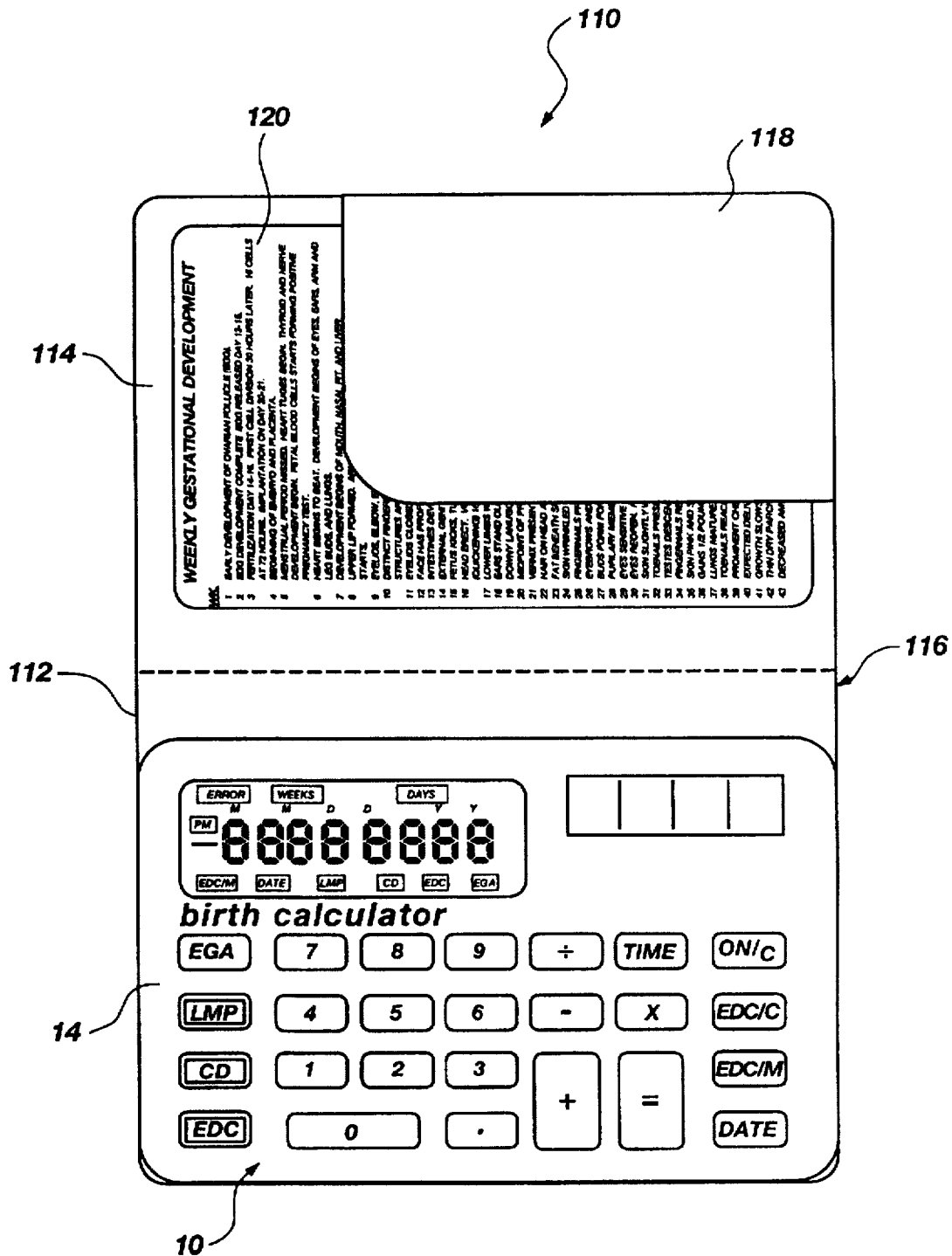
FIG. 3 is a plan view of the calculator of the invention in a carrying case.

FIG. 3 illustrates the calculator 10 of the present invention in a particularly suitable construction for easy portability and use. In particular, the calculator 10 is secured to a carrying case 110 comprising a first half 112 and a second half 114. The calculator 10 is secured to the first half 112 and the second half 114 may be folded over at fold point 116 to cover and enclose the calculator 10. The second half 114 of the carrying case 110 may preferably be constructed with a pocket 118 in which an instruction sheet or other written materials 120 may be stored. As here illustrated, the written materials 120 comprise a reference list of important and notable gestational development observances on a weekly basis. The written materials 120 are shown enlarged in FIG. 5.

Figure 4:
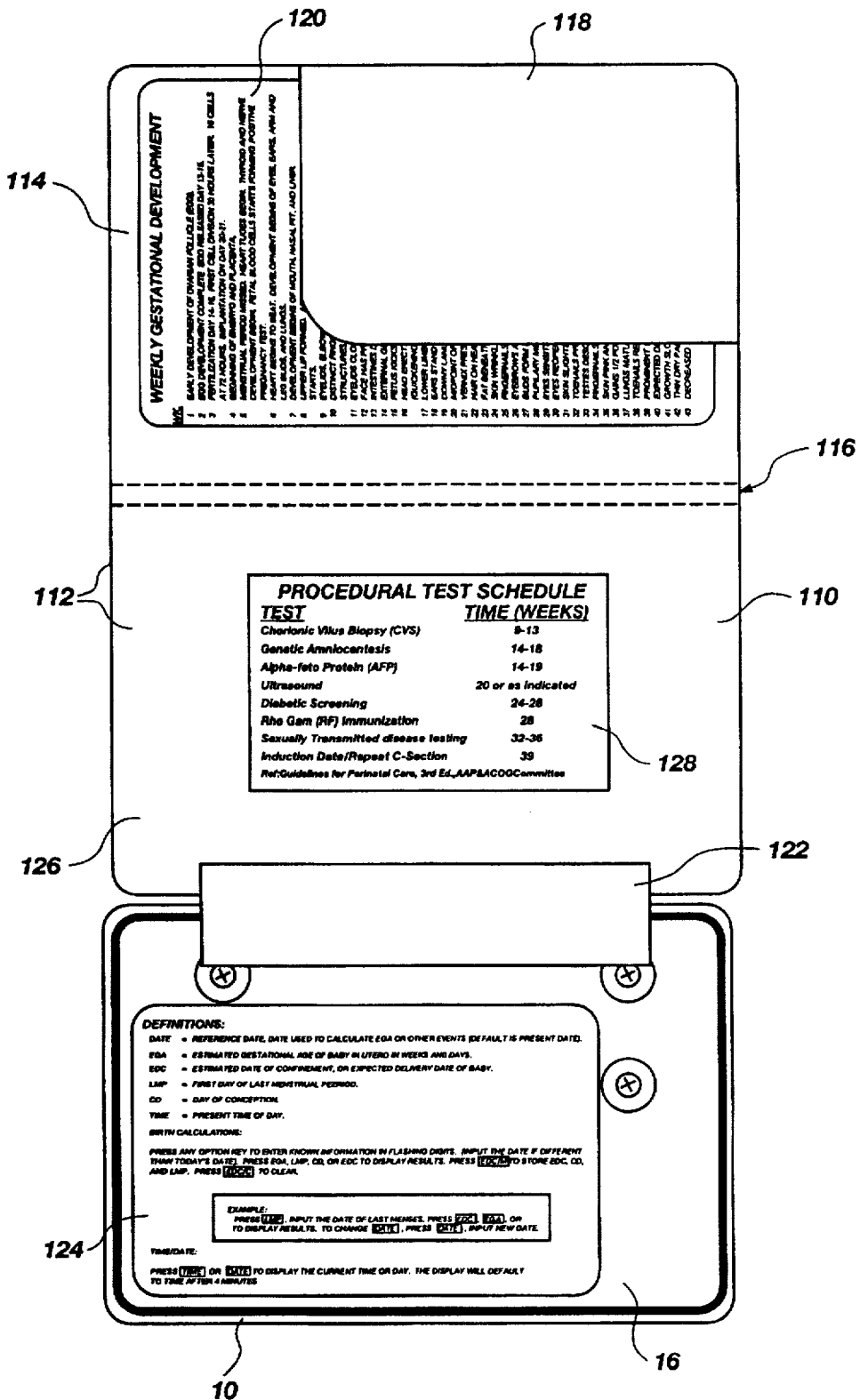
FIG. 4 is plan view of the calculator shown in FIG. 3 illustrating the placement of other information in the carrying case portion.

As shown in FIG. 4, the calculator 10 may be secured to the first half 112 of the carrying case 110 by a flap means 122 which permits the calculator 10 to be rotated out of adjacent position with the first half 112 of the carrying case 110, thereby exposing the back panel 16 of the calculator 10 for insertion of a new battery. As also illustrated, the back panel 16 of the calculator 10 may be used to imprint operating instructions 124, or other information. Likewise, the inner surface 126 of the first half 112 of the carrying case 110 may be used to display certain information 128, here shown as a schedule of important test dates which should be scheduled once the important gestational dates are established through use of the calculator, including, for example, a genetic amniocentesis (at 14–18 weeks), a chorionic villus biopsy (at 9–13 weeks), an ultrasound (at 20 weeks or later), a diabetic screening (at 24–28 weeks), and so forth.

The calculator 10 is programmed to calculate the important dates of pregnancy or gestational term based on the input of certain data. The important dates of the gestational term in humans are the LMP, CD, EDC and EGA. With the additional use of a reference date (RD) (also referred to herein as "DATE"), the entry into the calculator of any one or more variables of the five (i.e., RD, LMP, CD, EDC and EGA) results in the automatic calculation of the other three variables. Three linear equations can be used to calculate any of the five variables based upon entry of one or more of those variables. The equations are as follows:

EDC=LMP+280 (days)     [Equation 1]

EGA=DATE−LMP          [Equation 2]

CD=LMP+14(days) [Equation 3]

The reference date (RD) is automatically defaulted to the date upon which the data entry is made (i.e., the current date is always updated automatically by the calculator). However, any other relevant date may be entered as the reference date, as explained further in the specific examples given hereinafter. Thus, for example, accepting the current date as the RD and entering the LMP provides two of the five variables, and calculation of the other three variables can be made using the equations above. The dates entered and calculated are stored in memory and may be recalled accordingly. The dates may also be amended from time to time and stored again in memory by changing one or more variables, such as the RD.

Figure 6:
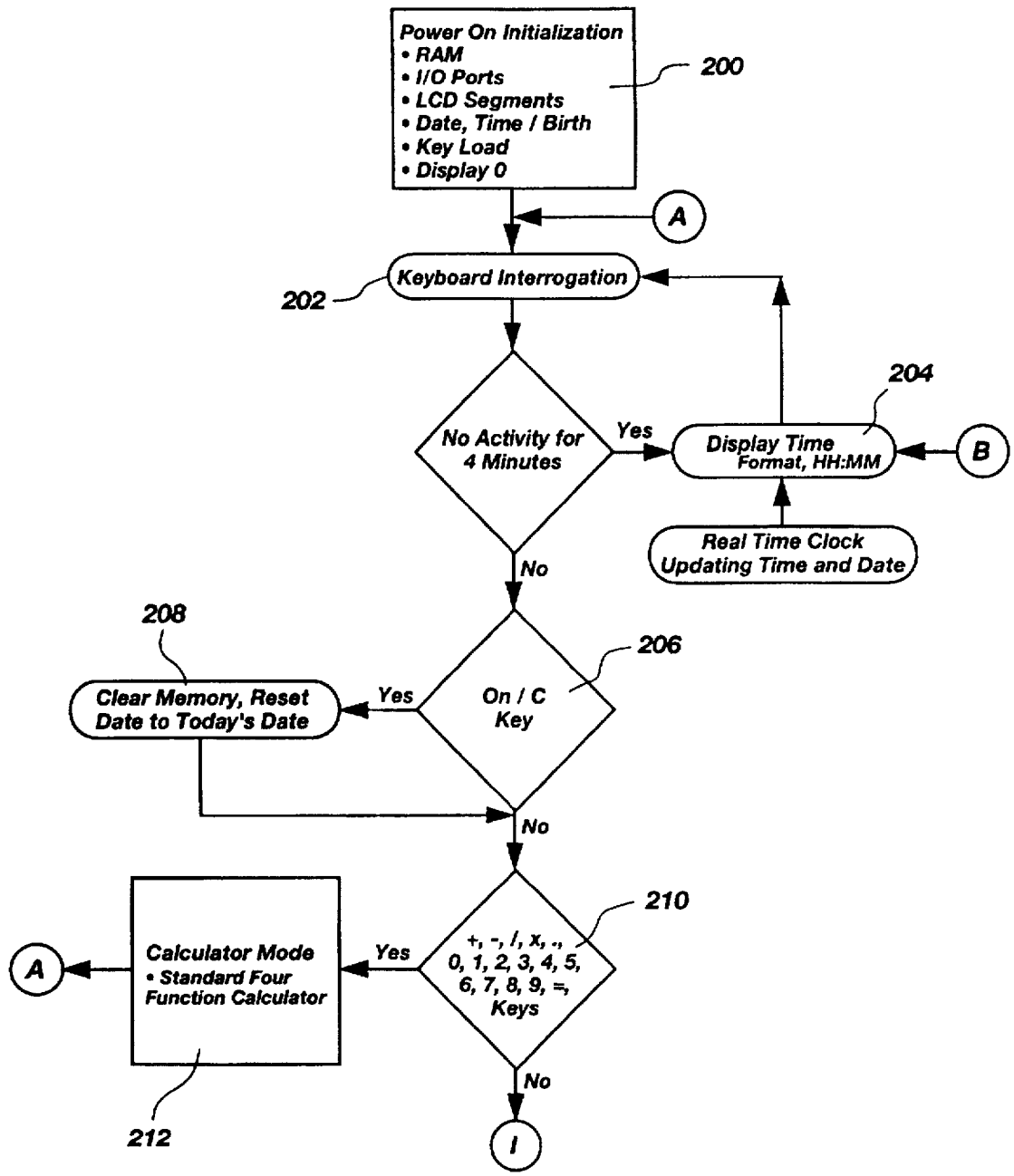
FIG. 6 is a flow diagram of the initial operation of the present invention.

As illustrated in FIG. 6, the calculator 10 is placed in operational mode 200 by pressing the "ON/C" key 30 which initiates the RAM, LCD display and other functions and memory of the calculator 10. Operation of the calculator 10 may then begin by undertaking some manner of keyboard interrogation 202, such as entering data or using the mathematical functions of the calculator. If no buttons are pushed, or no data is entered within four minutes, the LCD display 18 will automatically indicate the current time 204.

Although the calculator perpetually keeps the correct time and date, the time and date may be entered or updated, if necessary, at this point, as described hereinafter. If, for example, the "ON/C" key 30 is depressed again 206, the depression of the key 30 will clear the memory of the calculator and reset the RD to the current date, generally at 208. If the calculator is not to be used immediately for calculating obstetric dates, then depression of any mathematical function key 24 or a number on the keypad 22, generally at 210, will initiate the calculator 10 for use in the calculator mode 212. Notably, at any time during use of the calculator for determining obstetric dates, the calculator may be switched to mathematical calculation mode by depressing any mathematical function key 24.

Figure 7:
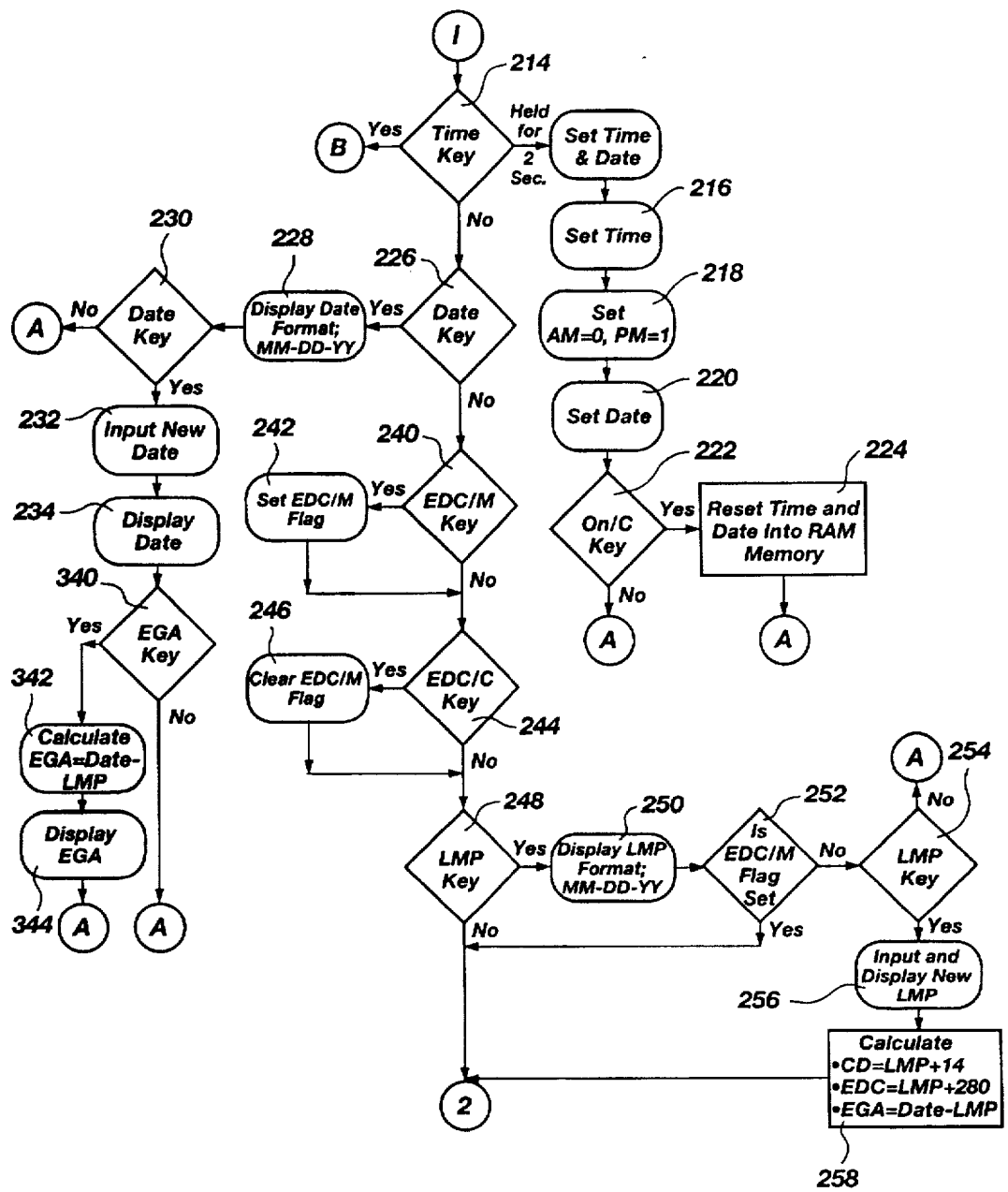
FIG. 7 is a continuing flow diagram of the flow diagram shown in FIG. 6, illustrating the input of variables and calculation of other relevant gestational dates.

The time and date in the memory of the calculator 10 may be initially established or reset, as illustrated in FIG. 7, by depressing the TIME key 28 and holding it for at least two seconds 214. The LCD display 18 will flash "HH-MM" as a prompt to enter the time. The time is set 216 by depressing the proper numbers on the keypad to enter the current hour and current minutes. The display advances as the numbers are entered. The "PM" icon will remain flashing until set to the correct portion of the day 218 by depressing "0" to set the time at "AM" or by depressing "1" to set the time at "PM".

The LCD display then flashes "MM-DD-YY" as a prompt to set or reset the date 220. The appropriate numbers on the keypad 22 are depressed until the month, day and year are entered. Notably, the "MM" portion of the date is programmed to accept any number from 1 through 12. If, for example, the number "2" is first entered, the number will automatically be entered as the second month. The "DD" portion of the display is programmed to accept any number from 1–31, depending on the month entered. If the number "3" is entered as the first digit of the date in month "02" (February), the number is automatically entered as the third day. Likewise, if the number "4" is entered as the first digit of the day in any month, the number is automatically entered as the fourth day of the month. The "YY" portion of the date is programmed to accept any number between 00 and 99. Entry of the number 50–99 may correspond, at present, to 1950 to 1999. Entry of the number 00–49 corresponds to 2000 to 2049. Depression of the "ON/C" key 222 following entry of the date sets the time and date entered in the memory 224.

If, when the calculator 10 is powered on, the time displayed is correct, the DATE key 56 may be depressed 226 to determine what date is stored in memory. The date retrieved from memory shows in the LCD display 228. If the date displayed from memory is incorrect or requires some revision, the DATE key may be depressed again 230 and the new date entered 232 following the steps (216–222) described previously. The new date will then be displayed 234 in the LCD display 18.

After the time and date are set, as necessary, the calculator may be used to calculate the important obstetric dates, as illustrated in FIGS. 6 and 7. The ON/C key 30 is pushed to initialize the program and clear the memory. At this point the memory automatically encodes the LMP, CD and EDC as "01-01-00" and the EGA as "0-0". Those default dates in memory will appear in a flashing mode in the LCD display 18 if any one of the variable function keys 26 is pushed, along with the icon corresponding to the variable function key 26 which was depressed. The DATE (RD) is automatically defaulted to the current date. Alternatively, the RD may be reset following the steps previously described.

If the obstetric dates have been previously determined and entered into memory, depressing the EDC/M key 54, generally at 240 in FIG. 7, will display the EDC/M icon 242 and will fix the calculated obstetric dates of LMP, CD and EDC in memory. Those dates will be displayed in the LCD display 18 upon depression of the respective variable function key. If the calculated dates are not to be kept, or the EDC/M is to be cleared, the EDC/C key 52 may be depressed 244. Depressing the EDC/C key clears the EDC/M icon and permits the entry of new data for LMP, CD, EGA and EDC. As illustrated in FIG. 7, if the EDC/C key is depressed 244, but the EDC/M icon is not cleared, then depression of one of the variable function keys 248, such as the LMP key, will display the LMP from memory 250. However, if the EDC/M icon is not displayed 252, then the memory has been cleared and the LMP key must be depressed again 254 to re-enter the LMP information anew 256. Following entry of the new LMP information and upon depression of any other variable function key (e.g., EDC, CD, EGA), the other variables are automatically calculated by the calculator 258 and may be stored in memory.

Figure 8:
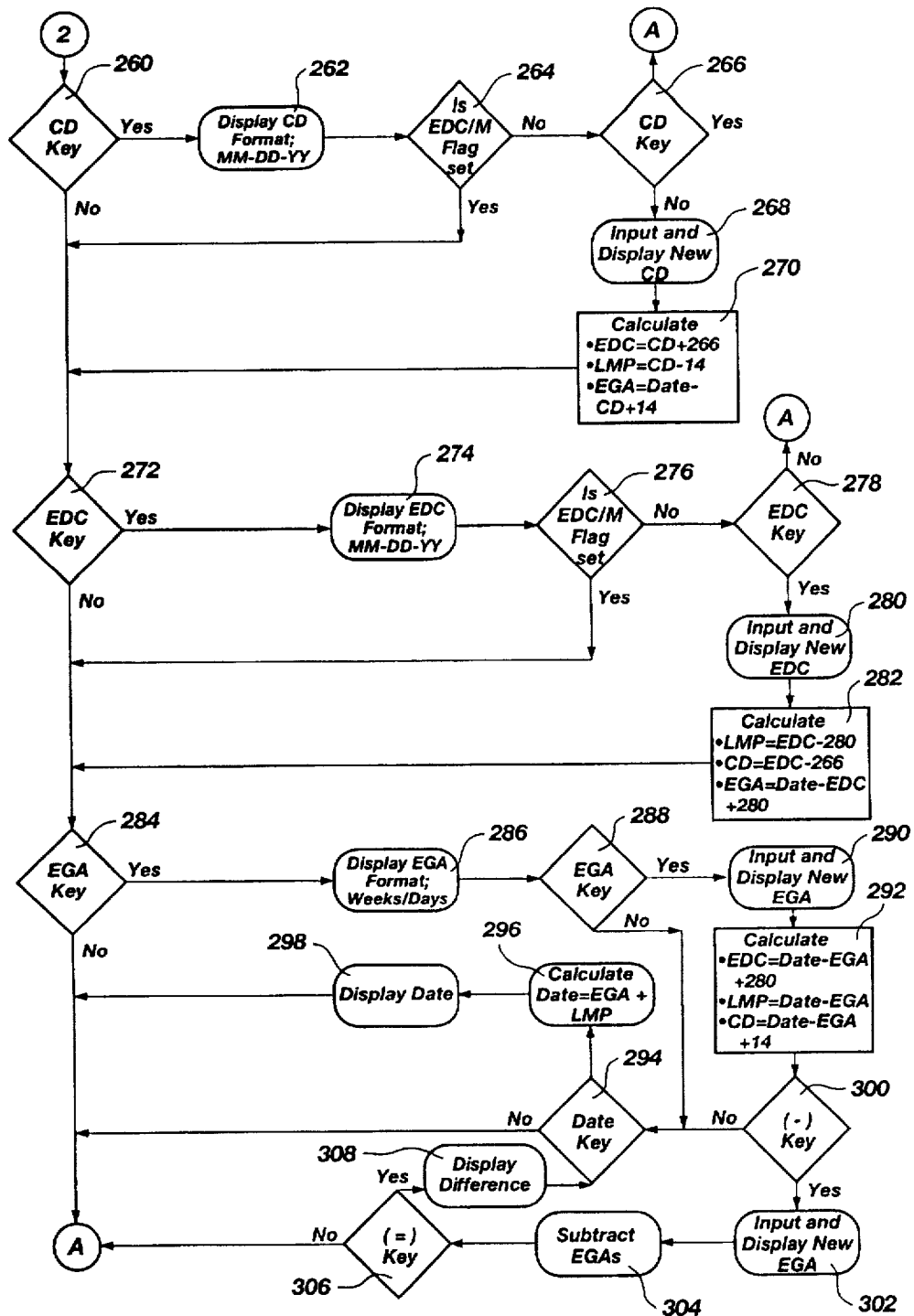
FIG. 8 is a continuing flow diagram of the flow diagram shown in FIG. 6, illustrating the calculation of still other variables of information.

In similar fashion, as illustrated in FIG. 8, once the RD has been set to a specific date (or the current date is used as the default RD), then depressing the CD key 260 will display a given date 262 in the LCD display. If the EDC/M icon is illuminated 264, then the date displayed is that which was retrieved from memory. If the EDC/M icon is not illuminated (or has been cleared by depression of the EDC/C key as described previously), then depression of the CD key 266 will initiate the ability to enter new data and have the new date appear in the display 268. Depressing any other variable function key will cause the program to calculate the other three variables 270, as shown, and the obstetric dates thus calculated may be entered in memory.

As also shown in FIG. 8, once the RD has been set, the EDC key may be depressed 272 to display the EDC date 274. Again, if the EDC/M icon is illuminated 276, the EDC date displayed in the LCD display 18 is from memory. However, if the EDC/M icon in not illuminated, then the EDC key may be depressed again 278 to permit the entry of new data 280 and the new date will appear in the LCD display 18. Depressing any other variable function key will then cause the calculator to automatically calculate the other three variables 282, and the calculated obstetric dates may be entered in memory.

Likewise, as shown in FIG. 8, the EGA key may be depressed 284 to display the EGA in the format of weeks and days 286. Depression of the EGA key 288 again will permit the entry of new data for the EGA and the newly input data in weeks and days will appear in the LCD display 290. Depression of any other variable function key will cause the calculator to automatically calculate the other variables 292 and those obstetric dates are entered in the memory. The calculator is electronically structured to permit the entry of another EGA, or a future procedural date in terms of weeks and days, by depressing the EGA key 288 again, followed by depression of the DATE key 294. The calculator will automatically calculate 296 and display 298 a new RD or date based on performing Equation 2, above. However, the previous information entered or calculated in connection with the DATE, LMP, CD and EDC will remain in memory and will not be altered by the newly entered EGA and recalculated RD. This capability permits the scheduling of procedural dates or other dates for patient observance (see EXAMPLE VI, hereinafter).

The difference between an EGA entered in the memory and a newly calculated EGA may be derived by depressing the substraction "−" key 300, followed by depression of the EGA key 44 again and entering a new EGA 302 in the manner previously described for data entry. Upon entry of the second EGA, the calculator will automatically subtract one EGA from the other EGA 304, and depression of the summation "=" key 306 provides a display of the difference between the two EGA's 308, displayed in the format of weeks and days. This calculation can be beneficial to determine the difference between a calculated EGA and an EGA based on empirical evidence derived from examination of the patient (e.g., an ultrasound) to enhance the accuracy of the calculated obstetric dates and to adjust, for example, for irregular menstrual periods. However, calculation of the difference between two EGA's, as described, does not affect or change the variable data in memory for the LMP, CD, EDC or DATE.

The uncertainty or variability that exists in menstrual cycles among individual patients may also be compensated for, or eliminated, by entering in the CD and calculating the other variables therefrom. By entering the known CD, the calculator may perform the equation:

$$EDC = CD + 266$$

to determine the EDC. Thus, more accurate calculations can be made when the conception date is known. That feature is particularly useful in in vitro fertilization procedures.

In addition to the calculations described above, if the DATE key is depressed 230 (FIG. 7) to input a new RD, followed by depression of the EGA key 340, the calculator will automatically recalculate the EGA 342 by performing Equation 2 and will display the newly calculated EGA 344. Changing the RD, and thus the EGA, will not affect or change the LMP, CD or EDC which is already entered in memory.

After data is entered and/or calculated based on the input of one or more variables, as previously described, that data can be removed from memory or replaced by either depressing the "ON/C" key or by depressing any variable function key in the manner previously described to enter new data and initiate recalculation of the missing variables. Further, if any variable function key other than DATE or EGA (i.e., LMP, CD, or EDC) is depressed following a calculation, the calculated date will be displayed along with the corresponding icon. If the variable function key is depressed a second time, the LCD display will flash as a prompt for the entry of new data. If new data is entered for that variable, the calculator will automatically zero out the data relating to the other variables when recalculation is initiated by the depression of any other variable function key. If, upon a second depression of the same variable function key, the date is not changed from that which exists in the memory, then the calculator will recalculate the other variables, but with no resulting change in the variables already entered into memory.

If an impermissible entry is attempted, such as entering the number 14 in the month (MM) display, the display will continue to flash until a valid number is entered. In addition, an ERROR icon may be illuminated if an illegal or undefined data entry is attempted.

The foregoing data entry and calculation capabilities of the present invention may be used to determine the important obstetric dates of a given pregnancy. Examples of the clinical situations in which the calculator may be used are as follows:

EXAMPLE I

In a conventional first obstetrical visit, the patient may know the beginning date of her last menstrual period. The physician may enter that date by pressing the LMP key, and using the current date as the RD, the other obstetric dates will be automatically calculated by the present invention. At that point, the EDC is known and appropriate tests may be scheduled for the patient.

EXAMPLE II

If the patient does not know the beginning date of her last menstrual period, the EGA may be determined by examining the uterine size and referring to the gestational age chart 120 included with the calculator. Using the current date as the RD, the EGA is entered and the calculator automatically calculates the remaining obstetrical dates.

EXAMPLE III

If other clinical tests may be used to establish any of the variables, then those variables may be used in calculating the other dates. For example, if the patient has undergone an ultrasound and the ultrasound results are used in the conventional manner to estimate an EGA, then the date the ultrasound was performed may be entered as the RD and the EGA determined from the ultrasound data may be entered as the second variables. The other three variable will be automatically calculated by the present invention.

EXAMPLE IV

With each return visit of the patient, new test data may be used to update any one of the variables, particularly EGA and EDC. Therefore, as new information becomes available, the date of the office visit may be entered as the RD and the new information relating to EGA or EDC may be entered to update the other obstetric dates with ever increasing accuracy. Further, the updated obstetric dates may be used to schedule future tests or to calculate a date of induction.

EXAMPLE V

With respect to infertility patients, the calculator of the present invention may be used in connection with patients who are taking prescribed medication to induce ovulation. Thus, the RD may be entered as the date of ovulation and the EGA at ovulation would be calculated as two weeks from a supposed last menstrual period. That information may then be used to calculate the EDC.

EXAMPLE VI

To schedule procedural tests or to determine other notable dates in the future, the EGA key may be depressed once to recall the calculated EGA, then depressed a second time to enter, in terms of weeks and days, a future date to be observed. Then pressing the DATE key will calculate and display the date in the future when that future event to be observed will fall. For example, based upon the EGA recalled from memory, and further calculated from the subsequent entry into the calculator of the time period "35 4 " (i.e., 35 weeks and 4 days), the calculator will display a day, month and year some 35 weeks in the future when the patient should cease flying in airplanes.

The calculator of the present invention may be used effectively to monitor the progress of obstetric patients through pregnancy by calculating in a very effective and accurate manner the important dates of a pregnancy or gestational period. The calculator of the present invention may be used not only to calculate and store the important dates of pregnancy, but may be used to accept and store in memory information relating to a specific patient's medical profile, such as blood type and relevant medical information (e.g., grava/para numbers), emergency telephone numbers, scheduling dates for performance of standard tests, and calculation of "safe sex" periods to avoid pregnancy. The calculator may even be adapted with database capabilities to provide such information as vitamin requirements for the patient and fetus, recommended food for the patient and fetus, and development schedules for such events as immunization shots and the like.

The structure and electronic capabilities of the present invention may be modified to meet the demands of the particular application. Hence, reference herein to specific details of the illustrated embodiments is by way of example and not by way of limitation. It will be apparent to those skilled in the art that many additions, deletions and modifications to the illustrated embodiments of the invention may be made without departing from the spirit and scope of the invention as defined by the following claims.

What is claimed is:

1. An electronic calculator for determining obstetric information comprising:

a housing;

a microcomputer housed within said housing and programmed for calculation of a plurality of obstetrical data responsive to selective input of at least one variable data value;

power means for operating said microcomputer housed within said housing;

at least one LCD display means oriented externally to said housing for viewing information;

depressible variable function keys positioned relative to said housing providing for entry of multiple variable obstetric data values in addition to a variable of last menstrual period and a variable of estimated gestational age for calculation of other variable obstetric data values therefrom; and a numerical keypad positioned relative to said housing and having depressible keys.

2. The electronic calculator of claim 1 further comprising random access memory, at least two kilobytes of read only memory and an LCD driver.

3. The electronic calculator of claim 2 further comprising means for accessing from said random access memory a plurality of obstetrical data calculated and stored therein, and program means for re-calculating said plurality of obstetrical data responsive to the selective input of at least one variable data value.

4. The electronic calculator of claim 3 further comprising program means for calculating the difference between said stored obstetrical data and said selectively input variable data values.

5. The electronic calculator of claim 3 further comprising memory storage capacity and memory accessing capability to calculate and store obstetrical information relating to more than one patient.

6. The electronic calculator of claim 2 further comprising depressible mathematical function keys positioned relative to said housing.

7. The electronic calculator of claim 1 wherein said power means comprises a battery and solar power means.

8. The electronic calculator of claim 7 further including a carrying case providing means for securing said housing thereto, said carrying case being structured with means for providing placement of written reference material therein.

9. The electronic calculator of claim 1 wherein said electronic calculator is sized and dimensioned for holding in a user's hand.

10. An electronic calculator for determining obstetric information comprising:

a housing;

a microcomputer housed within said housing and programmed for calculation of a plurality of obstetrical data responsive to selective input of at least one variable data value;

power means for operating said microcomputer housed within said housing;

at least one LCD display means oriented externally to said housing for viewing information;

depressible variable function keys positioned relative to said housing providing for entry of multiple variable data values for calculation of other variable obstetric data values therefrom, said variable function keys including a key for entering and accessing data relating to the last menstrual period and a key for entering and accessing data relating to an estimated gestational age; and a numerical keypad positioned relative to said housing and having depressible keys.

11. The electronic calculator of claim 10 further including a key for entering and accessing data relating to a date of conception.

12. The electronic calculator of claim 11 wherein said variable function keys further include a key for entering and accessing a reference date.

13. The electronic calculator of claim 12 wherein said variable function keys further include a key for entering and accessing an estimated date of confinement.

14. The electronic calculator of claim 10 wherein said variable function keys further include a key for entering and accessing a reference date.

15. A method of electronically calculating obstetrical dates comprising the steps of providing an electronic calculator having input, mathematical calculation, memory and display capabilities;

entering into said electronic calculator information relating to any variable selected from the group of variables consisting of:

beginning date of last menstrual period;
conception date;
estimated date of confinement;
estimated gestational age; and
reference date; and initiating calculation by said electronic calculator of at least one other of said variables from said group of variables.

16. The method of claim 15 further comprising the step of storing said entered variables and said calculated variables into said memory of said electronic calculator.

17. The method of claim 16 further comprising the steps of:

re-entering into said electronic calculator information relating to at least one of said variables from said group of variables; and initiating re-calculation by said electronic calculator of said other variables based on said re-entered information relating to said at least one of said variables.

18. The method of claim 16 further comprising the steps of:

re-entering information relating to said estimated gestational age variable; and initiating re-calculation of said reference date by said electronic calculator to obtain a new reference date based on said re-entered information relating to an estimated gestational age and said stored third, fourth and fifth variables, said stored reference date and said stored third, fourth and fifth variables remaining unchanged in said memory.

19. The method of claim 18 further comprising the steps of:

initiating the subtraction by said electronic calculator of said stored estimated gestational age variable from a re-entered estimated gestational age;

re-entering information relating to said estimated gestational age variable;

initiating calculation of the difference between said stored estimated gestational age variable and said re-entered information relating to said estimated gestational age variable; and displaying said difference between said stored estimated gestational age variable and said re-entered information relating to said estimated gestational age variable, said stored variables of estimated gestational age, last menstrual period, conception date, estimated confinement date and reference date remaining unchanged in memory.

20. The method of claim 16 further comprising the steps of:

accessing from memory the estimated gestational age;

entering into said electronic calculator information relating to a future date to be observed relative to the gestational term of a patient, said information being entered in terms of weeks and days;

initiating calculation by said electronic calculator of a date corresponding to said information relating to a future date; and displaying said calculated date in terms of a month, day and year.

21. The method of claim 15 further comprising the steps of: entering into said electronic calculator information relating to a second variable selected from said group of variables following entry of said a first variable; and initiating calculation by said electronic calculator of the third, fourth and fifth remaining variables from said group of variables.

22. The method of claim 21 wherein said first variable entered is a reference date, and said second variable entered is said estimated gestational age, said calculator determining through said calculation said third, fourth and fifth remaining variables.

23. The method of claim 22 further comprising the steps of: re-entering a reference date into said electronic calculator; and initiating the re-calculation of said estimated gestational age by said electronic calculator based on said re-entered reference date and said third, fourth and fifth variables stored in memory.

24. The method of claim 15 wherein said entered one variable selected from said group of variables is the conception date.

25. The method of claim 15 further comprising the steps of:

entering into said electronic calculator information relating to a patient's medical profile; and storing said entered information into said memory.

* * * * *